(12) United States Patent
Hight, III (10) Patent No.: US 6,361,751 B1
(45) Date of Patent: Mar. 26, 2002

(54) APPARATUS AND METHOD FOR DISINFECTING AN ENDOSCOPE

(75) Inventor: H. Thomas Hight, III, Kennesaw, GA (US)

(73) Assignee: Next Step Medical Technologies L.L.C., Kennesaw, GA (US)

( * ) Notice: Subject to any disclaimer, the term of this patent is extended or adjusted under 35 U.S.C. 154(b) by 0 days.

(21) Appl. No.: 09/702,465

(22) Filed: Oct. 31, 2000

Related U.S. Application Data (60) Provisional application No. 60/162,779, filed on Nov. 1, 1999.

(51) Int. Cl.$^7$ ............................. A61L 2/00; B08B 3/00
(52) U.S. Cl. ..................... 422/292; 422/294; 422/297; 422/300; 422/301; 422/934; 134/170
(58) Field of Search ............................ 422/28, 42, 292, 422/294, 297, 300, 301, 934, 36; 134/170

(56) References Cited

U.S. PATENT DOCUMENTS

| | | | |
|---|---|---|---|
| 3,956,011 A | 5/1976 | Carleton | 134/21 |
| 3,983,996 A | 10/1976 | Hendren, III | 206/363 |
| 4,288,882 A * | 9/1981 | Takeuchi | 15/88 |
| 4,496,522 A * | 1/1985 | McConnell | 422/300 |
| 4,730,729 A | 3/1988 | Mönch | 206/370 |
| 4,748,007 A * | 5/1988 | Gaudion et al. | 422/300 |
| 4,763,678 A * | 8/1988 | Ott | 134/171 |
| 4,923,061 A | 5/1990 | Trombley, III | 206/364 |
| 4,997,084 A | 3/1991 | Opie et al. | 206/364 |
| 5,061,246 A | 10/1991 | Anapliotis | 604/171 |
| 5,090,433 A | 2/1992 | Kamaga | 134/169 |
| 5,091,343 A * | 2/1992 | Schneider et al. | 422/297 |
| 5,165,503 A * | 11/1992 | Hoffman | 184/55.1 |
| D335,925 S | 5/1993 | Newman | D24/128 |
| 5,405,587 A * | 4/1995 | Fernandez et al. | 422/292 |
| 5,415,157 A | 5/1995 | Welcome | 128/4 |
| 5,425,815 A * | 6/1995 | Parker et al. | 134/26 |
| 5,529,750 A * | 6/1996 | Kochte | 422/28 |
| 5,534,221 A | 7/1996 | Hillebrenner et al. | 422/33 |
| 5,558,841 A * | 9/1996 | Nakagawa et al. | 422/105 |
| 5,738,824 A | 4/1998 | Pfeifer | 422/3 |
| 5,840,251 A * | 11/1998 | Iwaki | 422/36 |
| 5,882,589 A * | 3/1999 | Mariotti | 422/28 |

* cited by examiner

Primary Examiner—Elizabeth McKane
Assistant Examiner—Monzer R. Chorbaji
(74) Attorney, Agent, or Firm—Thomas, Kayden, Horstemeyer & Risley L.L.P.

(57) ABSTRACT

The present invention provides an apparatus for disinfecting an endoscope with a disinfecting solution, and that minimizes the surface area and air exposure of the disinfecting solution. In architecture, the endoscope disinfecting apparatus includes a disinfecting basin, an endoscope body section, an insertion tube section and a basin lid. The disinfecting basin is for disinfecting the air/water and light tube of the endoscope. The endoscope body section is for disinfecting a body and eye piece of the endoscope, and is connected to the disinfecting basin. The insertion tube section is connected to the endoscope body section and is for disinfecting a insertion tube of the endoscope. A basin lid connects to the disinfecting basin and provides a watertight seal over the disinfecting basin.

23 Claims, 8 Drawing Sheets

APPARATUS AND METHOD FOR DISINFECTING AN ENDOSCOPE

CROSS REFERENCE TO RELATED APPLICATIONS

This application claims the benefit of U.S. Provisional Application Serial No. 60/162,779 filed on Nov. 1, 1999, and entitled "Endoscope Soaking Basins" which is incorporated by reference herein in its entirety.

TECHNICAL FIELD

The present invention is generally related to endoscopes, and more particularly, is related to an apparatus and method for disinfecting an endoscope.

BACKGROUND OF THE INVENTION

Recent improvements in endoscope technology have provided great advances in the practice of medicine. These advances in endoscope technology have enabled medical practitioners to increase the ability to research patient conditions and aid in the diagnosis of heretofore difficult to diagnose conditions. Once the difficult to diagnose conditions are identified, the correct medical treatment can be applied with confidence. In addition to diagnostic applications, endoscopes are used to treat a growing number of conditions.

Endoscopes are widely used on a large variety of organs in the human body. These organs include, but are not limited to, digestive, respiratory, urinary, gynecological, orthopedic and otorhinolaryngological systems. The endoscopes used on these various organs of the human body are so expensive that they cannot simply be discarded after a single use on a single patient, but instead must be applied successfully to many patients. Therefore, the used endoscope must be thoroughly cleaned and disinfected before being available for use on another patient.

Currently, there are two types of endoscope cleaning and disinfecting apparatuses and methods. The first is generally utilized in well-financed operations, such as big hospitals. These well-financed institutions generally use an automatic cleaning and disinfecting endoscope machine costing several thousand dollars. The automatic cleaning and disinfecting machine operates much like a dishwasher in cleaning and disinfecting the endoscope. These machines can be costly to operate and repair.

The second type of endoscope cleaning apparatus is a soaking basin. The soaking basin type endoscope cleaning apparatus utilizes a basin to soak an endoscope in a nontoxic cleaning solution, followed by soaking the endoscope in a toxic disinfecting solution. The soaking basins are usually box shaped containers, with lids. The toxic disinfecting solution is typically glutaraldehyde. There are numerous problems with using glutaraldehyde. The used and discarded solution is toxic to the environment. The larger the quantity of glutaraldehyde used in the disinfecting process, the more the environmental damage from the discarded solution. Decreasing the quantity of glutaraldehyde needed for this process would benefit the environment.

While being used for soaking the instruments, glutaraldehyde evaporates, creating noxious and toxic fumes. Endoscope cleaning staff must wear badges monitoring their exposure to glutaraldehyde fumes. In order to try to limit human exposure to these toxic fumes, ventilation hoods with air removal fans are used. Despite provision of the hoods and fans, many endoscope cleaning and disinfecting rooms still smell strongly of glutaraldehyde.

The process of evaporation is related to several factors, one being the surface area of the liquid in contact with the air. Box shaped soaking basins in current use allow evaporation because of the relatively large liquid surface area. Decreasing the liquid surface area would lower the rate of evaporation and therefore decrease human exposure to these toxic fumes. Thus, a heretofore unaddressed need exists in the industry to address the aforementioned deficiencies and inadequacies.

SUMMARY OF THE INVENTION

The present invention provides an apparatus for disinfecting an endoscope with a disinfecting solution, which minimizes the surface area and air exposure of the disinfecting solution. Briefly described, the endoscope disinfecting apparatus includes a disinfecting basin, an endoscope body section, an insertion tube section, and a basin lid. The disinfecting basin is for disinfecting the air/water and light tube of the endoscope. The endoscope body section is for disinfecting a body and eye piece of the endoscope, and is connected to the disinfecting basin. The insertion tube section is connected to the endoscope body section and is for disinfecting a insertion tube of the endoscope. A basin lid connects to the disinfecting basin and provides a watertight seal over the disinfecting basin.

Other features and advantages of the present invention will become apparent to one with skill in the art upon examination of the following drawings and detailed description. It is intended that all such additional features and advantages be included herein within the scope of the present invention.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Reference will now be made in detail to the description of the invention as illustrated in the drawings. Although the invention will be described in connection with these drawings, there is no intent to limit it to the embodiment or embodiments disclosed therein. On the contrary, the intent is to include all alternatives, modifications, and equivalents included within the scope of the invention as defined by the appended claims.

Figure 1A:
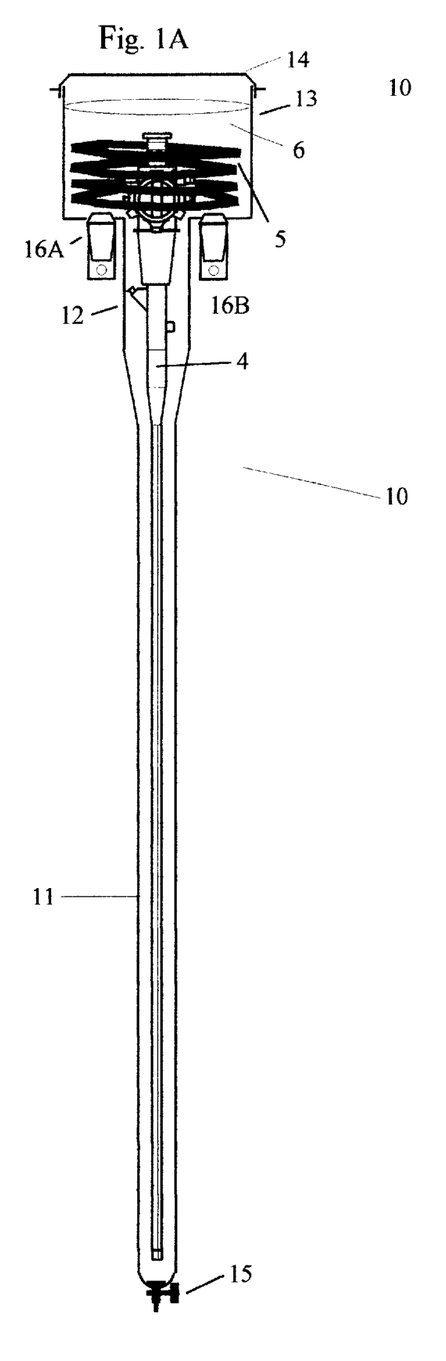
FIG. 1A is a side view of an endoscope within the endoscope disinfecting apparatus of the present invention.

Illustrated in FIG. 1A is a cutaway side view of one example of the endoscope disinfecting apparatus 10 of the present invention. The endoscope disinfecting apparatus 10 comprises many different sections to provide for disinfecting of an endoscope 4 by soaking it in a disinfecting solution. In the configuration shown, the endoscope disinfecting apparatus 10 is able to minimize the surface area and air exposure of the disinfecting solution 6. The endoscope disinfecting apparatus 10 enables an endoscope 4 to be disinfected by soaking the endoscope 4 in a disinfecting solution 6. The endoscope disinfecting apparatus 10 normally comprises an insertion tube section 11, an endoscope body section 12, a basin 13, a basin lid 14, and a drain 15. The insertion tube section 11 is designed in the general shape, size, and length corresponding to the type of endoscope for which the endoscope disinfecting apparatus 10 is specifically designed. The insertion tube section 11 length ranges from a few centimeters to over 200 centimeters long, depending on the length of the endoscope for which the endoscope disinfecting apparatus 10 is specifically designed to disinfect. The diameter of the insertion tube section will range from ¼ inch to the three to four inch range.

The endoscope disinfecting apparatus 10 is further comprised of body section 12 that is connected to the insertion tube section 11. The body section 12 supports the body of the endoscope 4. The endoscope body section 12 can be configured in a range of shapes and diameters, each shape and diameter designed specifically for the intended endoscope 4. The diameter of the body of the endoscope control section (12 in FIG. 1A) can range from one quarter inch to 5 inches, but will most commonly be ¾ inch to three inches (at least on human endoscopes).

The disinfecting basin 13 is attached to the endoscope body section 12 of the endoscope disinfecting apparatus 10. The endoscope basin 13 is specifically designed to reduce the liquid surface area exposure of the disinfectant 6 to reduce the rate of evaporation of the disinfecting solution 6. The disinfecting basin 13 can be configured in a wide variety of shapes and sizes corresponding to the type of endoscope 4 for which it is designed. The general diameter of disinfecting basin 13 can range from 4 inch to 18 inches, but preferably is 4 inches to 10 inches. The disinfecting basin has a depth of 2 inches to 10 inches, but preferably 4 inches to 8 inches.

To further reduce evaporation of the disinfecting solution 6, the endoscope disinfecting apparatus 10 further includes a basin lid 14. This basin lid 14 connects with a water tight seal to the basin 13. This lid 14 further prevents evaporation and spills of any toxic disinfectant solution 6 and thereby protects medical staff.

The endoscope disinfecting apparatus 10 further includes a draining valve 15 attached at the far end of the insertion tube section 11. The drain valve 15 enables medical staff to quickly and efficiently drain the disinfecting solution 6 from the endoscope disinfecting apparatus 10. It is also contemplated by the inventor that the drain valve 15 may be comprised of a drain plug or other type of mechanism to allow for controlled flow of the disinfecting solution 6 from the endoscope disinfecting unit 10. It is also contemplated by the inventor that the drain valve 15 may connect directly to some tube or other liquid containing mechanism to limit evaporation and further prevent medical staff from coming in direct contact with the disinfecting solution 6.

Further attached to the endoscope disinfecting apparatus 10 are mounting brackets 16A and 16B. These mounting brackets can attach to the endoscope disinfecting apparatus 10 on either side of the basin 13. The mounting brackets 16A and 16B are shown for purposes of illustration only, and in fact, may be any type of mounting mechanism to support the endoscope cleaning apparatus 10.

Figure 1B:
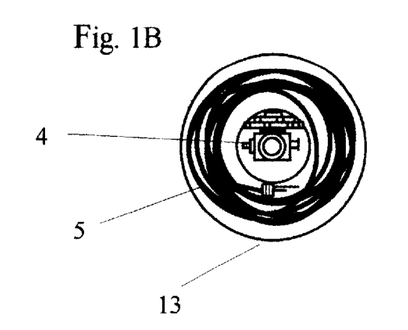
FIG. 1B is a top view of the endoscope within the endoscope disinfecting apparatus of the present invention, as shown in FIG. 1A.
Figure 1C:
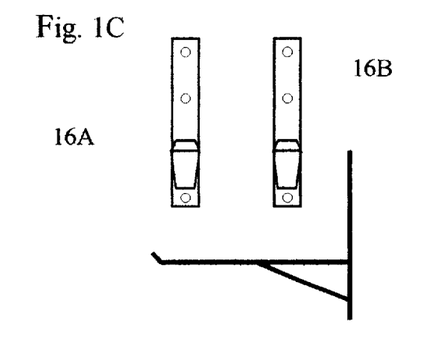
FIG. 1C is a diagram of the mounting brackets for supporting the endoscope disinfecting apparatus of the present invention, as shown in FIGS. 1A and 1B.

Illustrated in FIG. 1B is a top view of the endoscope disinfecting apparatus 10. As shown, the endoscope 4 is supported by the endoscope body section 12, the insertion tube 3 being suspended, allowing for maximum insertion tube surface contact with the disinfecting solution. The endoscope for air/water and light tube 5 is coiled within the basin 13. This enables the endoscope disinfecting apparatus 10 to soak and disinfect the insertion tube and the air/water and light tubes to further provide the cleanest possible endoscope 4 for use in a patient.

Figures 2A, 2B:
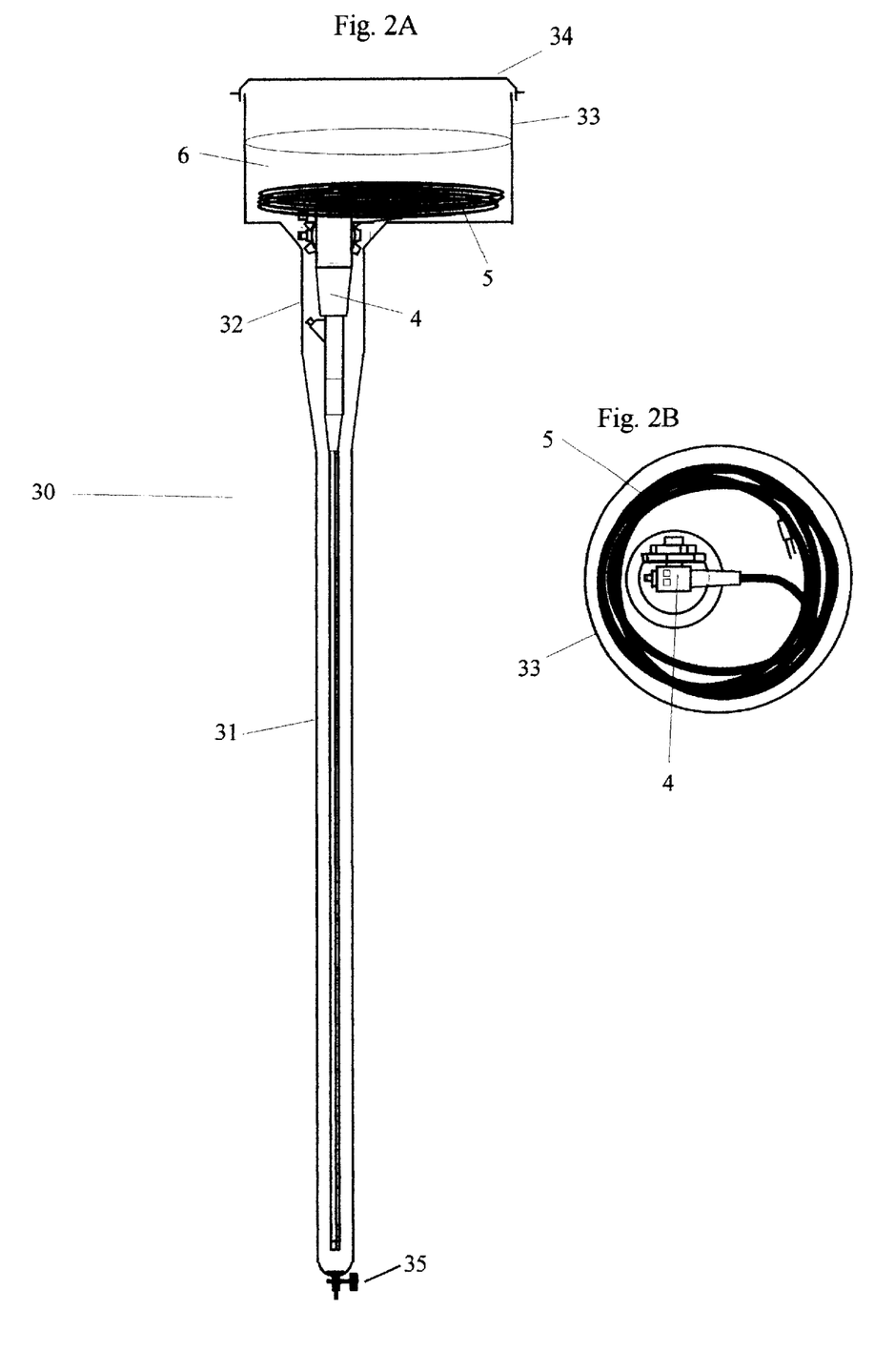
FIG. 2A is a side view of an alternative embodiment of the endoscope disinfecting apparatus.
FIG. 2B is a top view of the alternative embodiment of the endoscope cleaning apparatus, as shown in FIG. 2A.

Illustrated in FIG. 2A is another embodiment of the endoscope disinfecting apparatus 30 of the present invention. As shown, the endoscope disinfecting apparatus 30 is substantially similar to the illustration of the endoscope disinfecting apparatus 10 and the substantially similar features will not be discussed. However, the differences between the example endoscope disinfecting apparatus 10 and the endoscope disinfecting apparatus 30 will now be discussed. The first distinction is that the insertion tube section 31 is offset from the center of the basin 33. As shown previously in FIG. 1 with regard to the endoscope disinfecting apparatus 10, the insertion tube section 11 was centered with respect to the basin 13. Reflected in FIG. 2A is the embodiment of the endoscope disinfecting apparatus 30 with the insertion tube section 31 and endoscope body section 32 offset from the center of the basin 33. The offset of insertion tube section 31 from the center of basin 33 is used to allow for less flexible air/water and light tubes 5 to be coiled within the basin 33.

Illustrated in FIG. 2B is a top view that further demonstrates the insertion tube section 31 being offset from the center of basin 33. As shown, this is done to enable non-detachable and less flexible air/water and light tubes connected to the endoscope 4 to stay coiled within the basin 33 in order to allow the disinfecting operation to occur.

Figures 3A, 3B, 3C:
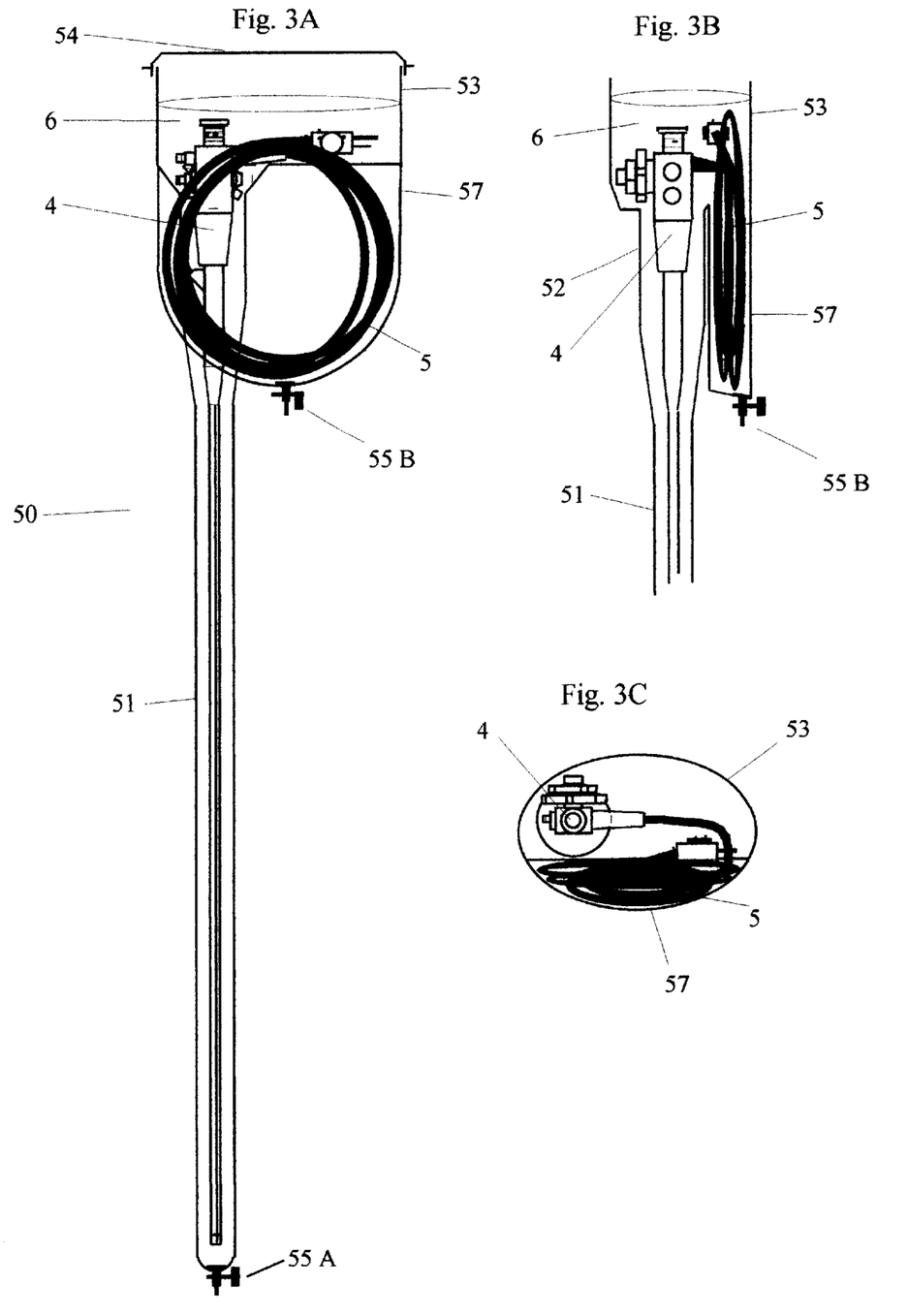
FIG. 3A is a side view of still another alternative embodiment for the endoscope disinfecting apparatus with a pouch for the air/water and light cord.
FIG. 3B is a different side perspective of an example of an alternative embodiment for the endoscope disinfecting apparatus with a pouch for supporting an air/water and light cord as shown in FIG. 3A.
FIG. 3C is a top view of the alternative embodiment for the endoscope disinfecting apparatus with a pouch for cleaning and disinfecting the air/water and light cord, as shown in FIGS. 3A and 3B.

Illustrated in FIG. 3A is still another alternative embodiment of the endoscope disinfecting apparatus 50 of the present invention. As discussed before, the endoscope disinfecting apparatus 50 is substantially similar to the endoscope disinfecting apparatus 10 previously discussed with regard to FIGS. 1A/1B and 2A/2B. However, the distinctions between FIGS. 1A/1B and 2A/2B will be herein discussed in detail. The first distinction of the endoscope disinfecting apparatus 50 is the addition of a pouch 57. The pouch 57 provides extra space to contain the air/water and light tube S that is connected to the endoscope 4 being disinfected in the endoscope disinfecting apparatus 50 of the present invention. By utilizing this pouch 57, the liquid surface area is further reduced as the air/water light tube 5 is coiled and turned downward. Also, less stress is put on the connection of the air/water light tube 5 with the endoscope 4.

Illustrated in FIG. 3B is another side view of the endoscope disinfecting apparatus 50 having a pouch 57. Here it is even more clearly illustrated that the air/water and light tube 5 is contained within a disinfecting solution 6, whereby the connection of the air/water light tube 5 and the endoscope 4 is not stressed. It is also depicted in FIG. 3B that the insertion tube section 51 is offset from the center of the basin 53. This offset is further implemented to relieve any stress on the connection of the air/water and light tube 5 with the endoscope 4. This is further shown in the top view of FIG. 3C wherein the endoscope 4 is inserted in the endoscope disinfecting apparatus 50 and offset from the center of the basin 53.

Figure 4A:
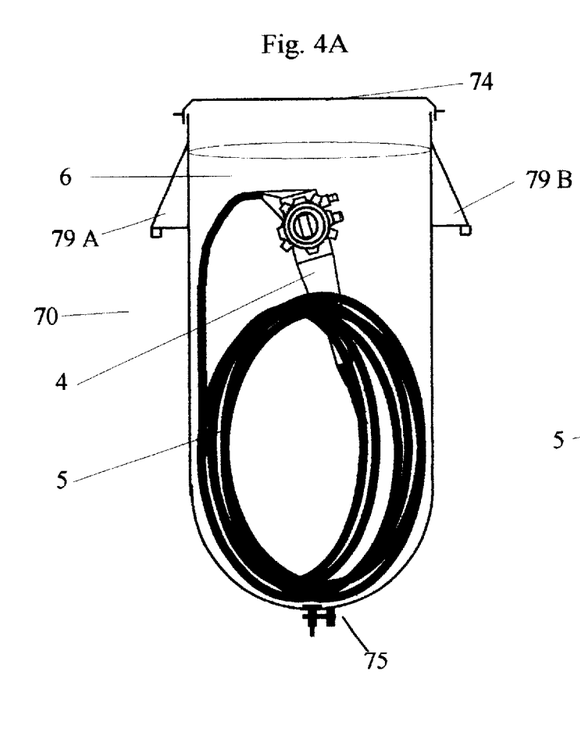
FIG. 4A is a side view of still another embodiment of the endoscope cleaning apparatus. In this alternative embodiment, the endoscope cleaning apparatus is in the shape of a thin U-shaped bucket.
Figure 4B:
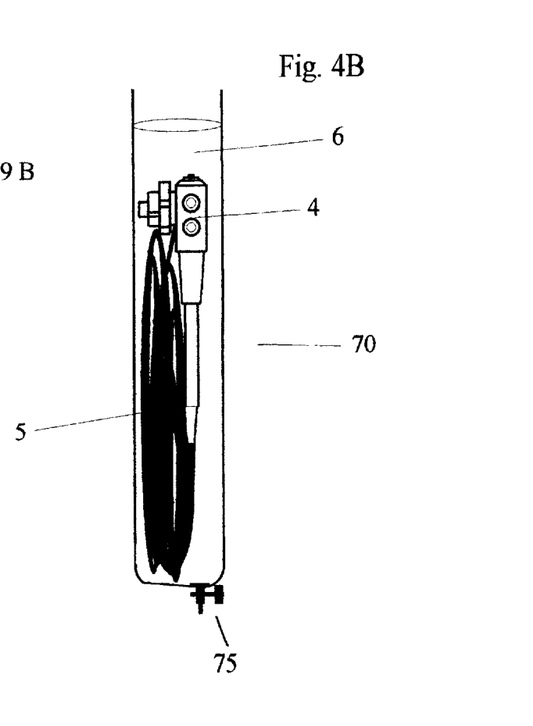
FIG. 4B is a still another side view of the alternative embodiment of the endoscope disinfecting apparatus, as shown in FIG. 4A.
Figure 4C:
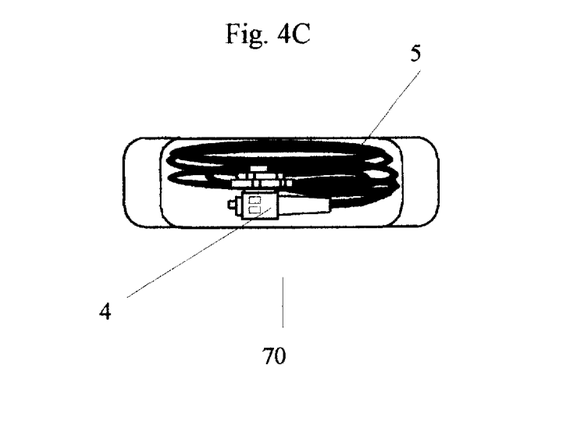
FIG. 4C is a top view of the alternative embodiment of the endoscope disinfecting apparatus, as shown in FIGS. 4A and 4B.

Illustrated in FIG. 4A is still another alternative embodiment of the endoscope disinfecting apparatus 70. As shown in FIG. 4A, the endoscope disinfecting apparatus 70 is shaped as a thin U-shaped bucket. This thin U-shaped bucket 70 includes a lid 74 to seal the U-shaped endoscope disinfecting apparatus 70 and prevent the disinfecting solution 6 or fumes from the disinfecting solution 6 to escape. The endoscope disinfecting apparatus 70 in the U-shaped bucket configuration is generally utilized when multiple types of endoscopes of different lengths are disinfected in the same lab and work space is not available to accommodate numerous basins each designed specifically for a certain shape and length and size of endoscope. The apparatus 70 can be wide enough to disinfect two or more endoscopes simultaneously. Shown in FIG. 4B is an example showing that the endoscope disinfecting apparatus 70 that is thinner in dimension than the U-shaped bucket 70 is wide. This further reduces the amount of disinfecting solution 6 required to disinfect the endoscope 4. Although endoscope disinfecting apparatus 70 does not reduce the liquid surface area as much as other alternative embodiments of this invention, it allows for ease of use where multiple endoscope types are being disinfected, while still significantly reducing the liquid surface area compared to the box type basins currently in use. FIG. 4C illustrates a top view of the endoscope disinfecting apparatus 70.

Figures 5A, 5B:
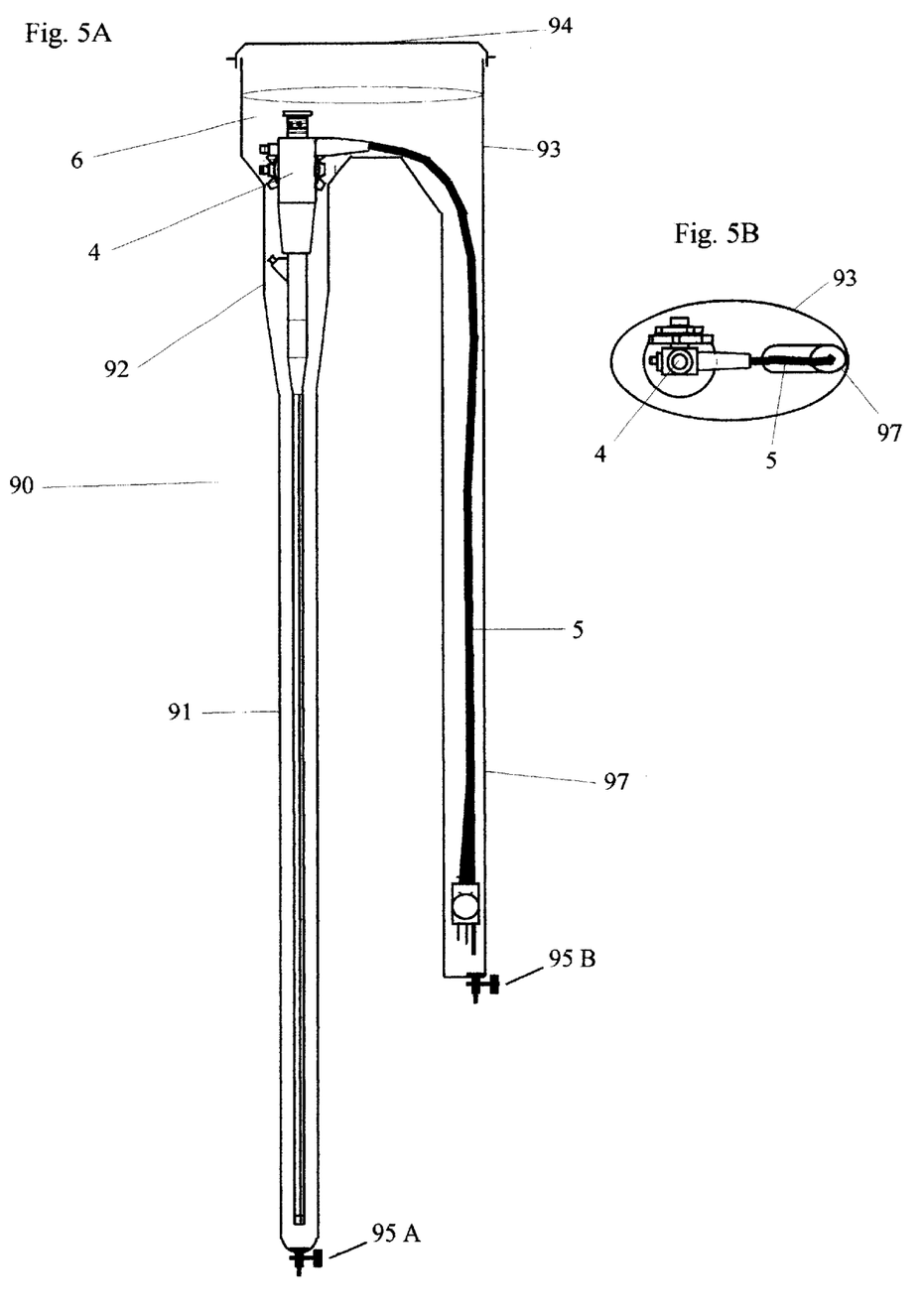
FIG. 5A is a side view of still another alternative embodiment of the endoscope disinfecting apparatus with a well for disinfecting the air/water and light tube.
FIG. 5B is a top view of the alternative embodiment of the endoscope disinfecting apparatus with the well for disinfecting the air/water and light tube, as shown in FIG. 5A.

Illustrated in FIG. 5A is still another alternative embodiment of the endoscope disinfecting apparatus 90 of the present invention. As shown, the endoscope disinfecting apparatus 90 utilizes an insertion tube section 91 and a body section 92 for supporting and protecting endoscope 4. The significant difference between the endoscope disinfecting apparatus 90 and the endoscope disinfecting 10 (FIG. 1A) is the addition of the universal tube section 97. The universal tube section 97 is the container for supporting and protecting the air/water and light tube 5 during the disinfecting operation. This alternative embodiment provides the capability of disinfecting the endoscope without putting any stress on the connection between the endoscope 4 and the air/water and light tube 5. Shown in FIG. 5B is a top view of the endoscope disinfecting apparatus 90 with the universal tube 97.

Figures 6A, 6B, 6C, 6D:
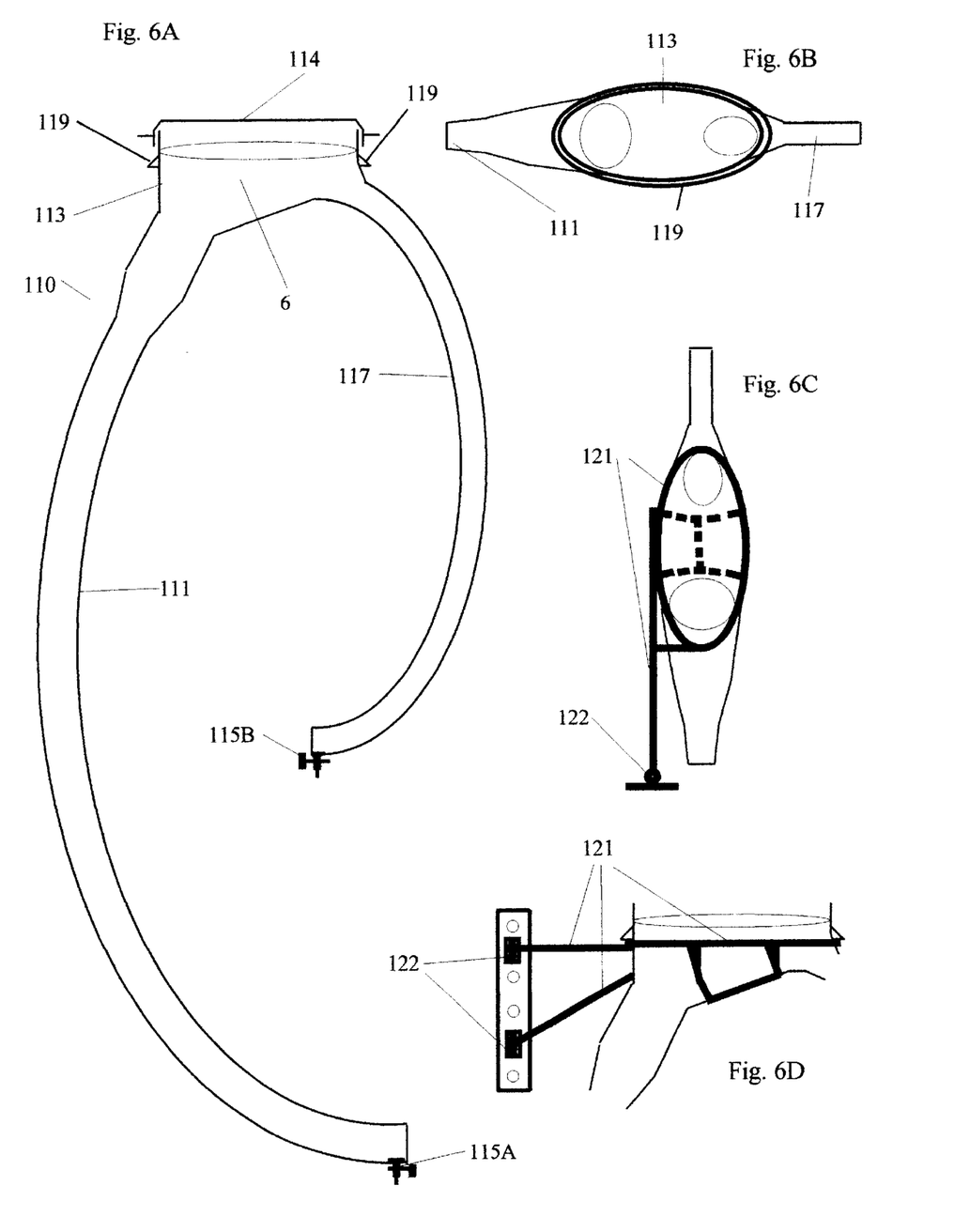
FIG. 6A is a side view of another embodiment comprising a hanging version of the endoscope disinfecting apparatus.
FIG. 6B is a top view of the alternative embodiment of the hanging endoscope disinfecting apparatus, as shown in FIG. 6A.
FIG. 6C is a top view of the hanging endoscope disinfecting apparatus shown in FIGS. 6A and 6B, as supported by a mounting bracket.
FIG. 6D is a side view of the hanging endoscope disinfecting apparatus as shown in FIGS. 6A–6C.

Illustrated in FIG. 6A is a hanging version of the endoscope disinfecting apparatus 110. The significant difference between the hanging endoscope disinfecting apparatus 110 and the endoscope disinfecting apparatus 90 (FIGS. 5A and 5B) is that the insertion tube section 111 and universal tube section 117 are curved to match the curvature of the endoscope 4 and air/water and light tube 5. The endoscope disinfecting apparatus 110 is curved so that longer endoscopes could be inserted more easily. The curve allows a shorter distance to the ground. The top of the basin 113 could be brought down to somewhere between elbow and shoulder level. The average 165 cm colonoscope is over 5 feet long. Also, the curve allows a slanted angle to put the scope in, easier especially for a shorter person. Also illustrated in FIG. 6A are drainage valves 115A and 115B that are positioned at the lowest point of the insertion tube section 111 and the universal tube section 117. This arrangement enables a medical staff member to drain the disinfecting solution 6 from the endoscope disinfecting apparatus 110 without moving or tipping the endoscope disinfecting apparatus 110. As discussed previously with regard to FIG. 1A, the drainage valves 115A and 115B could comprise any type of valve or plug for controlling the flow of disinfecting solution 6. It is also contemplated by the inventor that drainage valves 115A and 115B are connectable to a tube to further limit the medical staff from coming into contact with the disinfecting solution 6.

Illustrated in FIG. 6B is a top view of the curved endoscope disinfecting apparatus 110. Illustrated are the basin 113, the curved insertion tube section 111, and the curved universal tube section 117. Illustrated in FIGS. 6C and 6D are the top and side view of the curved endoscope disinfecting apparatus 110 and mounting bracket 121. It is contemplated by the inventor that the mounting bracket 121 for the endoscope disinfecting apparatus 110 would be a hinged unit that would allow the endoscope disinfecting apparatus 110 to be rotated closer to a wall or solid surface on hinges 122.

Figures 7A, 7B:
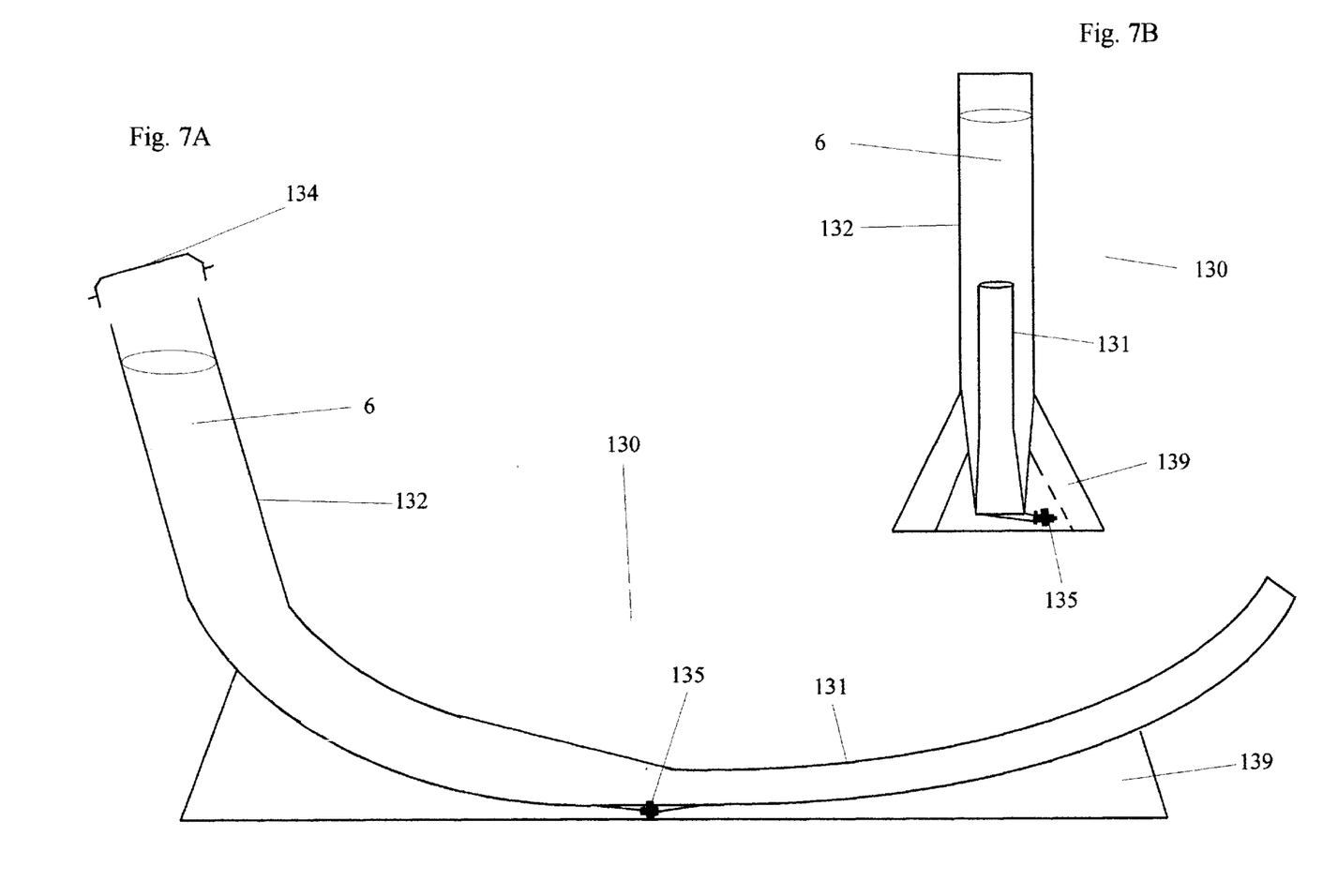
FIG. 7A shows an example of a desk top version of the endoscope disinfecting apparatus of the present invention.
FIG. 7B is a side view of the desk top embodiment of the endoscope disinfecting apparatus shown in FIG. 7A.

Illustrated in FIG. 7A is a desktop version of the endoscope disinfecting apparatus 130. As shown, the desk top model of the endoscope disinfecting apparatus can be curved with a curvature of to reduce required desk top work space. The desk top endoscope disinfecting apparatus has a body section 132 connected to an insertion tube section 131. The body section 132 and insertion tube section 131 are both supported by the desk top support 139. Connected to the endoscope disinfecting apparatus 130 is the drain valve 137. The drain valve 137 is connected to the lowest point of the endoscope disinfecting apparatus 130. Also illustrated is a cap 134 for closing off the endoscope disinfecting apparatus 130 to prevent the escape of any disinfecting solution 6 or disinfectant solution vapors. Illustrated in FIG. 7B is a side view of the desk top endoscope disinfecting apparatus 130.

Figure 8A:
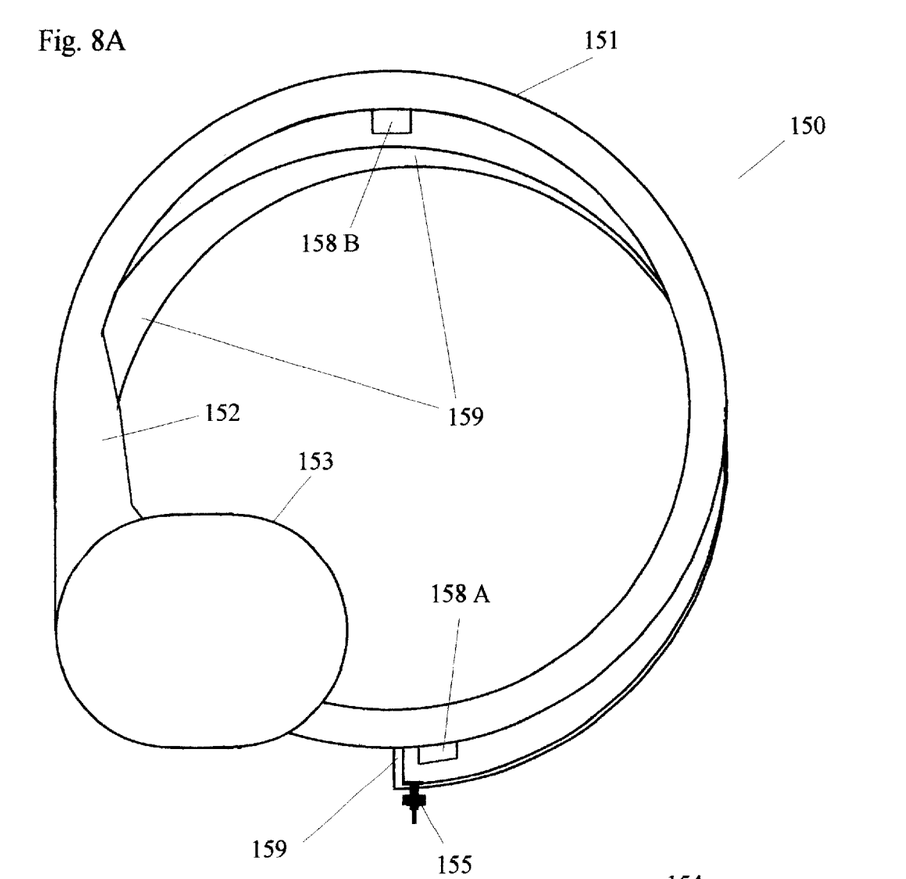
FIG. 8A is a top view of a coiled endoscope disinfecting apparatus of the present invention.

Illustrated in FIG. 8A is a top view of an alternative embodiment of the endoscope disinfecting apparatus 150. The coiled endoscope disinfecting apparatus 150 has a basin 153 connected to a body section 152. The body section 152 is further connected to the coiled insertion tube section 151. The outside diameter of the coiled endoscope disinfecting apparatus 150 ranges from a preferred range of 5 to 30 inches. Given one and three quarters coils as illustrated in FIG. 8A, an endoscope with a 220 centimeter insertion tube would require a diameter of about 17 inches across. A 160 cm insertion tube would require a diameter of about 13 inches across. A 65 cm insertion tube would require a diameter of about 10 inches. While the invention shows the insertion tube section 151 coiling one and three quarters times, it is contemplated by the inventor that the insertion tube section 151 may be coiled through one half to five turns. Attached at the lowest point of the coiled endoscope disinfecting apparatus 150 is the drain valve 157.

Figure 8B:
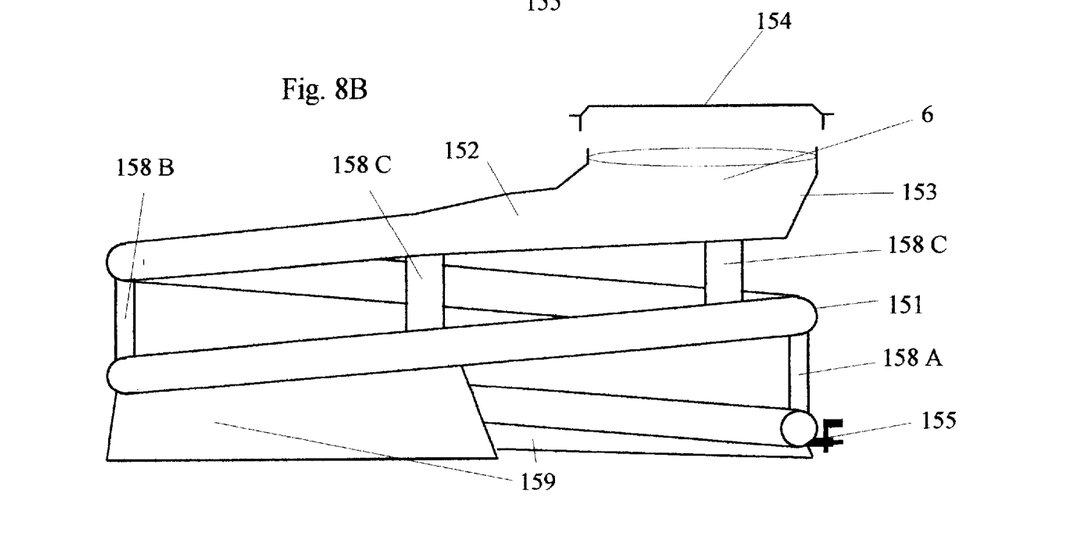
FIG. 8B is a side view of the coiled endoscope disinfecting apparatus as shown in FIG. 8A.

Illustrated in FIG. 8B is a side view of the coiled endoscope disinfecting apparatus 150. Shown is the lid 154 that is connectable to the body section 153. As stated before, the lid 154 enables a medical staff member to prevent the escape of any disinfecting solution 6 or vapors from the disinfecting solution. It is contemplated by the inventor that the enlargement of the basin 153 and body section 152 of the insertion tube section 151 would allow two or more endoscopes to be disinfected at the same time.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of the present invention and protected by the following claims.

I claim:

1. An endoscope disinfecting apparatus for disinfecting an endoscope with a disinfecting solution, that minimizes the surface area and air exposure of the disinfecting solution, said endoscope disinfecting apparatus comprising:
    a disinfecting basin that disinfects an air/water and light tube of the endoscope;
    an endoscope body section connected to said disinfecting basin that disinfects a body and eye piece of the endoscope;
    an insertion tube section connected to said endoscope body section that disinfects an insertion tube of the endoscope;
    a basin lid to provide a watertight seal over said disinfecting basin; and
    wherein said disinfecting basin is a pouch connected to a side of said endoscope body section.

2. The apparatus of claim 1, wherein said endoscope disinfecting apparatus is adapted to contain solution of glutaraldehyde.

3. The apparatus of claim 1, wherein said insertion tube section has a length ranging from 1 to 60 inches.

4. The apparatus of claim 1, wherein said insertion tube section has a diameter ranging from ¼ inch to 6 inches.

5. The apparatus of claim 1, wherein said endoscope body section has a diameter ranging from ¼ to 6 inches.

6. The apparatus of claim 1, wherein said endoscope body section has a length ranging from 2 to 10 inches.

7. The apparatus of claim 1, wherein said disinfecting basin has a diameter ranging from 4 to 10 inches.

8. The apparatus of claim 1, wherein said disinfecting basin has a depth ranging from 2 to 10 inches.

9. The apparatus of claim 1, wherein said endoscope disinfecting apparatus further comprises a drain.

10. The apparatus of claim 9, wherein said drain further comprises a drain valve.

11. The apparatus of claim 9, wherein said drain further comprises a drain plug.

12. The apparatus of claim 1, wherein said endoscope disinfecting apparatus further comprises:
    a mounting bracket configured to receive said endoscope disinfecting apparatus to hang said endoscope disinfecting apparatus.

13. The apparatus of claim 1, wherein said insertion tube section is concentric with said endoscope body section.

14. The apparatus of claim 1, wherein said insertion tube section is offcenter with said endoscope body section.

15. The apparatus of claim 1, wherein said insertion tube section is curved.

16. The apparatus of claim 15, wherein said disinfecting basin is curved.

17. The apparatus of claim 16, wherein said endoscope disinfecting apparatus further comprises a base to support said endoscope disinfecting apparatus on a surface.

18. The apparatus of claim 1, wherein said disinfecting basin has a length ranging from 12 to 30 inches.

19. An endoscope disinfecting apparatus for disinfecting an endoscope with a disinfecting solution, that minimizes the surface area and air exposure of the disinfecting solution, said endoscope disinfecting apparatus comprising:
    a disinfecting basin that disinfects an air/water and light tube of the endoscope;
    an endoscope body section connected to said disinfecting basin that disinfects a body and eye piece of the endoscope;
    an insertion tube section connected to said endoscope body section that disinfects an insertion tube of the endoscope;
    a basin lid to provide a watertight seal over said disinfecting basin; and
    wherein said disinfecting basin is a well connected to a side of said endoscope body section.

20. An endoscope disinfecting apparatus for disinfecting an endoscope with a disinfecting solution, that minimizes the surface area and air exposure of the disinfecting solution, said endoscope disinfecting apparatus comprising:
    a disinfecting basin that disinfects an air/water and light tube of the endoscope;
    an endoscope body section connected to said disinfecting basin that disinfects a body and eye piece of the endoscope;
    an insertion tube section connected to said endoscope body section that disinfects an insertion tube of the endoscope, wherein said insertion tube section is coiled; and
    a basin lid to provide a watertight seal over said disinfecting basin.

21. The apparatus of claim 20, wherein said disinfecting basin is curved.

22. The apparatus of claim 21, wherein said endoscope disinfecting apparatus further comprises a base to support said endoscope disinfecting apparatus on a surface.

23. The apparatus of claim 20, wherein said insertion tube section is coiled between ½ and 5 turns.

* * * * *